United States Patent
Hoover et al.

(10) Patent No.: US 10,544,259 B2
(45) Date of Patent: Jan. 28, 2020

(54) POLYCARBONATE WITH LOW CHLORINE CONTENT AND A METHOD OF MAKING AND ANALYZING THE SAME

(71) Applicant: SABIC GLOBAL TECHNOLOGIES B.V., Bergen op Zoom (NL)

(72) Inventors: James Franklin Hoover, Evansville, IN (US); Sasi Sethumadhavan Kannamkumarath, Evansville, IN (US); Peter Anthony DiMattia, Houston, TX (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 19 days.

(21) Appl. No.: 15/748,198

(22) PCT Filed: Aug. 31, 2016

(86) PCT No.: PCT/IB2016/055209
§ 371 (c)(1),
(2) Date: Jan. 29, 2018

(87) PCT Pub. No.: WO2017/037637
PCT Pub. Date: Mar. 9, 2017

(65) Prior Publication Data
US 2018/0215868 A1 Aug. 2, 2018

Related U.S. Application Data

(60) Provisional application No. 62/212,178, filed on Aug. 31, 2015.

(51) Int. Cl.
*C08G 64/06* (2006.01)
*C08G 64/24* (2006.01)
*G01N 33/44* (2006.01)

(52) U.S. Cl.
CPC ............ *C08G 64/24* (2013.01); *C08G 64/06* (2013.01); *G01N 33/442* (2013.01)

(58) Field of Classification Search
USPC .................................................. 528/198, 196
See application file for complete search history.

(56) References Cited

U.S. PATENT DOCUMENTS

| | | | |
|---|---|---|---|
| 4,798,767 A | 1/1989 | Aoki et al. | |
| 5,760,160 A | 7/1998 | Isshiki et al. | |
| 5,852,156 A | 12/1998 | Hachiya et al. | |
| 5,972,273 A | 10/1999 | Hachiya | |
| 6,462,165 B1 | 10/2002 | Ito et al. | |
| 6,833,096 B2 | 12/2004 | Wang et al. | |
| 2005/0209434 A1 | 9/2005 | Abad et al. | |
| 2005/0239996 A1 | 10/2005 | Kirchhoff et al. | |
| 2006/0063906 A1 | 3/2006 | Blaschke et al. | |
| 2012/0108782 A1 | 5/2012 | Konig et al. | |
| 2012/0157653 A1 | 6/2012 | Konig et al. | |
| 2013/0225763 A1 | 8/2013 | Pai-Paranjape et al. | |

FOREIGN PATENT DOCUMENTS

| | | |
|---|---|---|
| EP | 0709421 A1 | 5/1996 |
| EP | 0846713 A2 | 6/1997 |
| JP | 3399191 B2 | 8/1996 |
| JP | 3551211 A | 2/1997 |
| JP | 11310218 A | 11/1999 |
| JP | 2003040997 A | 2/2003 |
| WO | 0058072 A1 | 10/2000 |
| WO | 2005103114 A1 | 11/2005 |
| WO | 2008025446 A1 | 3/2008 |

OTHER PUBLICATIONS

International Search Report for International Application No. PCT/IB2016/055209; International Filing Date: Aug. 31, 2016; dated Jan. 4, 2017; 7 Pages.

Written Opinion of the International Searching Authority for International Application No. PCT/IB2016/055209; International Filing Date: Aug. 31, 2016; dated Jan. 4, 2017; 9 Pages.

*Primary Examiner* — Terressa Boykin
(74) *Attorney, Agent, or Firm* — Cantor Colburn LLP

(57) ABSTRACT

An aromatic polycarbonate, having an aromatic polycarbonate backbone, can comprise: less than or equal to 5 ppm of polymeric chlorine attached to the aromatic polycarbonate backbone; less than 0.5 ppm of dichloromethane, less than 5 ppm of monohydric phenols, and less than 0.5 ppm of aromatic compounds containing no chlorine based on the total weight of the aromatic polycarbonate, wherein the aromatic compounds are compounds other than the aromatic polycarbonate.

20 Claims, 4 Drawing Sheets

POLYCARBONATE WITH LOW CHLORINE CONTENT AND A METHOD OF MAKING AND ANALYZING THE SAME

CROSS REFERENCE TO RELATED APPLICATIONS

This application is a 371 of International Application No. PCT/IB2016/055209, filed Aug. 31, 2016, which claims priority to U.S. Application Ser. No. 62/212,178 filed Aug. 31, 2015 which are incorporated herein by reference in their entirety.

BACKGROUND

This disclosure relates to polycarbonate compositions, and in particular to polycarbonate compositions with low chlorine content, methods of manufacture, and uses thereof.

In the interfacial reaction process of polycarbonate, a carbonyl source such as phosgene is often reacted with a bisphenol A in the presence of an amine catalyst to produce bisphenol-A (BPA) polycarbonate, generating hydrogen chloride (HCl) as a by-product of the reaction. During this reaction, an alkali metal hydroxide, such as sodium hydroxide is generally co-added with the carbonyl source to neutralize the HCl. In that case, sodium chloride as a reaction by-product is dissolved in the aqueous reaction phase and can be removed to trace levels through washing.

The interfacial polymerization of polycarbonate can often result in polycarbonates with a high yellowness index, which can restrict the uses of those polymers from use, for example, in optical applications where a low yellowness index is needed.

Accordingly, an improved method for polymerizing polycarbonate and improved polycarbonate quality are desired.

BRIEF SUMMARY

Disclosed herein is a polycarbonate with low chlorine content and a method of making and of analyzing the same.

In an embodiment, an aromatic polycarbonate, having an aromatic polycarbonate backbone, comprises: less than or equal to 5 ppm of polymeric chlorine attached to the aromatic polycarbonate backbone; less than 0.5 ppm of dichloromethane, less than 5 ppm of monohydric phenols, and less than 0.5 ppm of aromatic compounds containing no chlorine based on the total weight of the aromatic polycarbonate, wherein the aromatic compounds are compounds other than the aromatic polycarbonate.

In an embodiment, a polycarbonate polymerization process, comprises: analyzing a chlorate content of an alkali metal hydroxide solution, and, if the chlorate content is greater than or equal to 20 ppm based on the total weight of the alkali metal hydroxide solution, then reducing the chlorate content in the alkali metal hydroxide solution to a value of less than or equal to 20 ppm chlorate based on the total weight of the alkali metal hydroxide solution prior to interfacially polymerizing; and interfacially polymerizing a phosgene and a dihydroxy compound in the presence of the alkali metal hydroxide solution and an interfacial catalyst to form the aromatic polycarbonate of any of Embodiments 19-20.

The above described and other features are exemplified by the following figure and detailed description.

BRIEF DESCRIPTION OF THE DRAWINGS

The following is a brief description of the drawings, which are exemplary of the various embodiments described herein.

FIG. 2 is a gas chromatography mass spectrometry (GC-MS) chromatogram of polycarbonate produced with NaOH having high chlorate content, where

DETAILED DESCRIPTION

Figure 1:
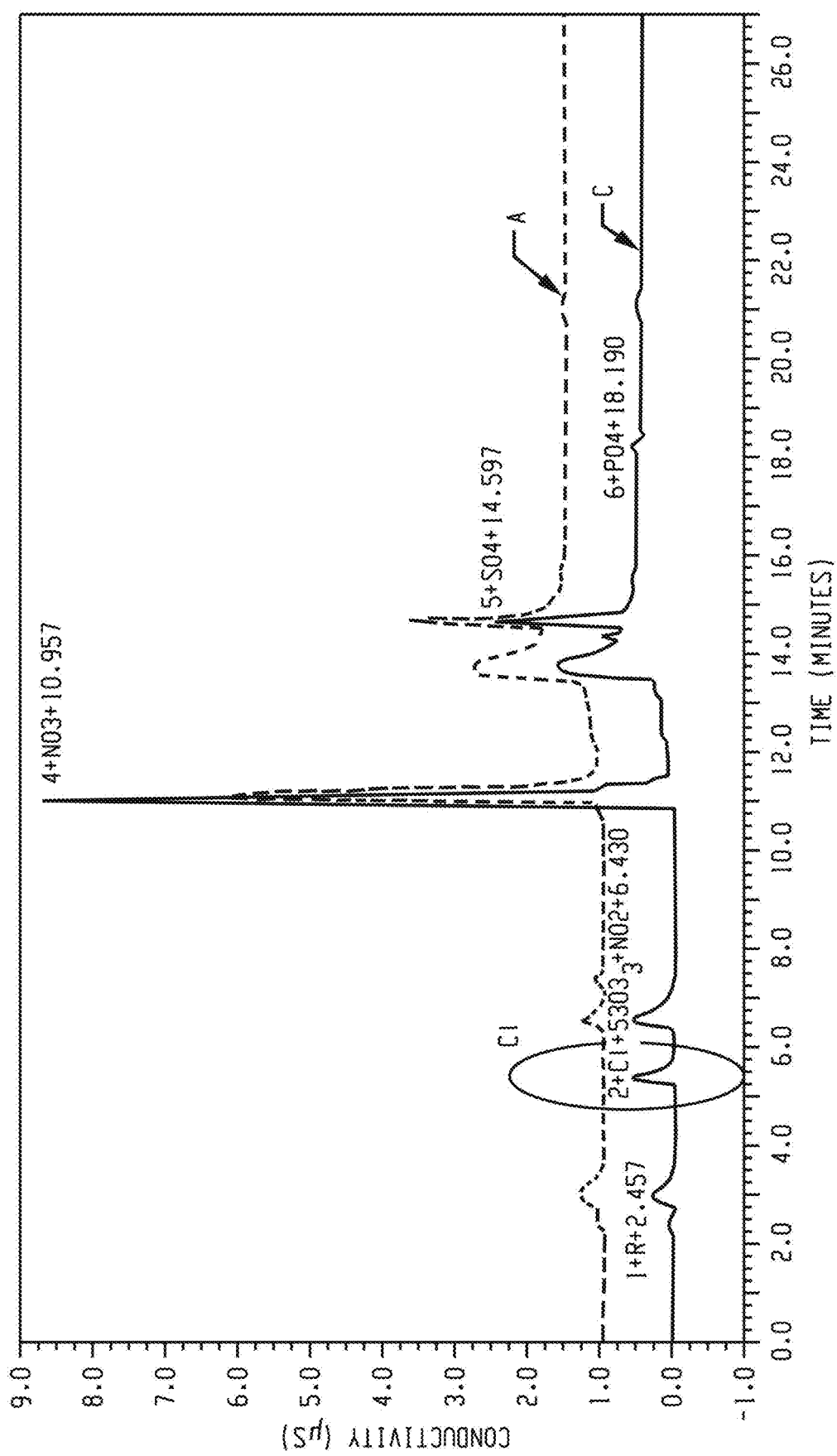
FIG. 1 is an ion chromatograph of separated polycarbonate produced with NaOH having varying chlorate content.

In the interfacial reaction process of polycarbonate, a carbonyl source such as phosgene is often reacted with a bisphenol A (BPA) in the presence of an amine catalyst to produce bisphenol-A polycarbonate, generating hydrogen chloride (HCl) as a by-product of the reaction. During this reaction, an alkali metal hydroxide, such as sodium hydroxide is generally co-added with the carbonyl source to neutralize the HCl. In that case, sodium chloride as a reaction by-product is dissolved in the aqueous reaction phase and can be removed to trace levels through washing.

It was surprisingly found that the presence of an alkali metal chlorate in the alkali metal hydroxide used in the polymerization can have an effect on the final polycarbonate. The presence of the alkali metal chlorate can be present in the alkali hydroxide as a by-product of the electrolysis reaction used to produce the alkali hydroxide. For example, it was discovered that sodium chlorate in a sodium hydroxide solution can result in chlorination of the BPA during or after polymerization; it can undesirably react with amine catalysts, such as triethylamine and trimethylamine catalysts; it can lead to the formation of highly reactive chlorammonium ions; or a combination comprising at least one of the foregoing can occur. For example, it was surprisingly found that these chlorammonium ions can readily chlorinate aromatic compounds, such as the BPA units of a polycarbonate backbone. The occurrence of one or more of the foregoing reactions can result in one or more of a high amine content, a high ionic chloride content, a polymeric chlorine (indicating chorine present in the polymer chain, for example, that reacted with an aromatic ring).

It was discovered that a high chloride and/or amine content can be detrimental to polycarbonate products and can also have undesirable effect on the manufacturing or processing systems. For example, it was found that a polycarbonate with high total chlorine content, for example, of greater than or equal to 25 parts per million by weight (ppm) with a high aromatic chlorine content (for example, of greater than or equal to 10, for example, greater than or equal to 60 ppm) and/or comprising a high content of chlorinated compounds such as methylene chloride (for example, of greater than or equal to greater than or equal to 5 ppm, specifically, greater than or equal to 10 ppm) can undesirably suffer from an increased yellowness index as compared to the same polycarbonate with a chlorine content of less than or equal to 50 ppm; wherein the ppm values are all based on the total weight of the polycarbonate. Additionally, polycarbonate with high total chloride content can result in corrosion of processing equipment, including extruders and molding machines, and/or can lead to HCl out-gassing from permanent installations of molded parts in close proximity to sensitive components.

Applicants have discovered that one or more of the above shortcomings can be rectified by controlling the total amount of alkali metal chlorate in the alkali metal hydroxide used in the interfacial polymerization. For instance, an aqueous solution comprising 20 to 50 weight percent (wt %), specifically, a 30 to 40 wt % that comprises less than or equal to 20 ppm alkali metal chlorate present in the solution can result in a polycarbonate with one or more of a reduced total chlorine content and/or a reduced polymeric chlorine content as compared to a polycarbonate prepared using the same polymerization conditions, but in the presence of a concentration of alkali metal chlorate of greater than 20 ppm. Specifically, the inventors hereof therefore developed a method of producing polycarbonate comprising analyzing a chlorate content of an alkali metal hydroxide solution, if the alkali metal hydroxide solution comprises greater than or equal to 20 ppm of a chlorate based on the total weight of the alkali metal hydroxide solution, then the process comprises reducing the chlorate in the alkali metal hydroxide solution to a value of less than or equal to 20 ppm chlorate based on the total weight of the alkali metal hydroxide solution prior to interfacially polymerizing, and interfacially polymerizing a carbonate compound and a dihydroxy compound in the presence of the alkali metal hydroxide solution and an interfacial catalyst to form a polycarbonate. The chlorate content of the alkali metal hydroxide solution can be measured, for example, by titration.

The polycarbonate prepared by this method can have less than or equal to 10 ppm polymeric chlorine, where the polymeric chlorine is present as chlorinated aromatic components in the polymer chain, or less than or equal to 5 ppm, or less than or equal to 3 ppm, or less than or equal to 2 ppm polymeric chlorine based on the total weight of the polycarbonate. The polycarbonate compositions can also have low levels of extractable ionic chloride, including less than or equal to 10 ppm extractable ionic chloride, or 2 ppm to 5 ppm extractable ionic chloride, or 2 ppm to 2.5 ppm extractable ionic chloride, based on the total weight of the composition.

The polycarbonate prepared by this method can have a Yellowness Index of a 100 mil (2.54 millimeter (mm)) thick molded plaque of less than or equal 1.5, more specifically, 1 to 1.5, or 1 to 1.3, or 1 to 1.1. The polycarbonate prepared by this method can have a Yellowness Index of a 100 mil (2.54 millimeter (mm)) thick molded plaque of less than or equal 1.6, or less than or equal 1.3, or 1 to 1.3, or 1.1 to 1.6. Yellowness Index (YI) as used herein is measured in accordance with ASTM D1925-70 (1988).

"Polycarbonate" as used herein means a polymer or copolymer having repeating structural carbonate units of formula (1)

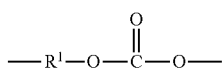

(1)

wherein at least 60 percent of the total number of $R^1$ groups are aromatic or each $R^1$ contains at least one $C_{6-30}$ aromatic group. Specifically, each $R^1$ can be derived from a dihydroxy compound such as an aromatic dihydroxy compound of formula (2) or a bisphenol of formula (3).

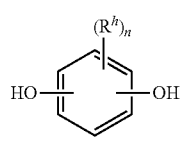

(2)

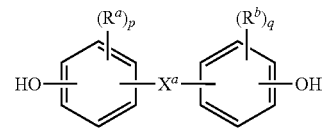

(3)

In formula (2), each $R^h$ is independently a $C_{1-10}$ hydrocarbyl group such as a $C_{1-10}$ alkyl or a $C_{6-10}$ aryl, and n is 0 to 4. The dihydroxy compound (also referred to as bisphenol) can be free of a halogenated dihydroxy compound, for example, the dihydroxy compound can comprise 0 to 0.1 wt % or 0 wt % of a halogenated dihydroxy compound based on the total weight of the dihydroxy compound.

In formula (3), $R^a$ and $R^b$ are each independently a $C_{1-12}$ alkoxy or $C_{1-12}$ alkyl; and p and q are each independently integers of 0 to 4, such that when p or q is less than 4, the valence of each carbon of the ring is filled by hydrogen. Accordingly, p and q can each be 0, or p and q can each be 1, and $R^a$ and $R^b$ can each be a $C_{1-3}$ alkyl group, specifically methyl, disposed meta to the hydroxy group on each arylene group. $X^a$ is a bridging group connecting the two hydroxy-substituted aromatic groups, where the bridging group and the hydroxy substituent of each $C_6$ arylene group are disposed ortho, meta, or para (specifically para) to each other on the $C_6$ arylene group, for example, a single bond, —O—, —S—, —S(O)$_2$—, —C(O)—, or a $C_{1-18}$ organic group, which can be cyclic or acyclic, aromatic or non-aromatic, and can further comprise heteroatoms such as oxygen, nitrogen, sulfur, silicon, or phosphorous. For example, $X^a$ can be a substituted or unsubstituted $C_{3-18}$ cycloalkylidene; a $C_{1-25}$ alkylidene of the formula —C($R^c$)($R^d$)— wherein $R^c$ and $R^d$ are each independently hydrogen, $C_{1-12}$ alkyl, $C_{1-12}$ cycloalkyl, $C_{7-12}$ arylalkyl, $C_{1-12}$ heteroalkyl, or cyclic $C_{7-12}$ heteroarylalkyl; or a group of the formula —C(=$R^e$)— wherein $R^e$ is a divalent $C_{1-12}$ hydrocarbon group.

Some illustrative examples of specific dihydroxy compounds include the following: bisphenol compounds such as 4,4'-dihydroxybiphenyl, 1,6-dihydroxynaphthalene, 2,6-dihydroxynaphthalene, bis(4-hydroxyphenyl)methane, bis(4-hydroxyphenyl)diphenylmethane, bis(4-hydroxyphenyl)-1-naphthylmethane, 1,2-bis(4-hydroxyphenyl)ethane, 1,1-bis (4-hydroxyphenyl)-1-phenylethane, 2-(4-hydroxyphenyl)-2-(3-hydroxyphenyl)propane, bis(4-hydroxyphenyl)phenylmethane, 1,1-bis (hydroxyphenyl)cyclopentane, 1,1-bis(4-hydroxyphenyl)cyclohexane, 1,1-bis(4-hydroxyphenyl)isobutene, 1,1-bis(4-hydroxyphenyl)cyclododecane, trans-2,3-bis(4-hydroxyphenyl)-2-butene, 2,2-bis(4-hydroxyphenyl) adamantane, alpha,alpha'-bis(4-hydroxyphenyl)toluene, bis (4-hydroxyphenyl)acetonitrile, 2,2-bis(3-methyl-4-hydroxyphenyl)propane, 2,2-bis(3-ethyl-4-hydroxyphenyl)propane, 2,2-bis(3-n-propyl-4-hydroxyphenyl)propane, 2,2-bis (3-isopropyl-4-hydroxyphenyl)propane, 2,2-bis(3-sec-butyl-4-hydroxyphenyl)propane, 2,2-bis(3-t-butyl-4-hydroxyphenyl)propane, 2,2-bis(3-cyclohexyl-4-hydroxyphenyl)propane, 2,2-bis(3-allyl-4-hydroxyphenyl)propane, 2,2-bis(3-methoxy-4-hydroxyphenyl)propane, 4,4'-dihydroxybenzophenone, 3,3-bis(4-hydroxyphenyl)-2-butanone, 1,6-bis(4-hydroxyphenyl)-1,6-hexanedione, ethylene glycol bis(4-hydroxyphenyl)ether, bis(4-hydroxyphenyl)ether, bis(4-hydroxyphenyl)sulfide, bis(4-hydroxyphenyl)sulfoxide, bis(4-hydroxyphenyl)sulfone, 2,7-dihydroxypyrene, 6,6'-dihydroxy-3,3,3',3'-tetramethylspiro(bis)indane ("spirobiindane bisphenol"), 3,3-bis(4-hydroxyphenyl)phthalimide, 2,6-dihy- droxydibenzo-p-dioxin, 2,6-dihydroxythianthrene, 2,7-dihydroxyphenoxathin, 2,7-dihydroxy-9,10-dimethylphenazine, 3,6-dihydroxydibenzofuran, 3,6-dihydroxydibenzothiophene, and 2,7-dihydroxycarbazole; resorcinol, substituted resorcinol compounds such as 5-methyl resorcinol, 5-ethyl resorcinol, 5-propyl resorcinol, 5-butyl resorcinol, 5-t-butyl resorcinol, 5-phenyl resorcinol, 5-cumyl resorcinol, or the like; catechol; hydroquinone; substituted hydroquinones such as 2-methyl hydroquinone, 2-ethyl hydroquinone, 2-propyl hydroquinone, 2-butyl hydroquinone, 2-t-butyl hydroquinone, 2-phenyl hydroquinone, 2-cumyl hydroquinone, 2,3,5,6-tetramethyl hydroquinone, 2,3,5,6-tetra-t-butyl hydroquinone, or the like.

Specific dihydroxy compounds include resorcinol, 2,2-bis (4-hydroxyphenyl) propane ("bisphenol A" or "BPA", in which each of $A^1$ and $A^2$ is p-phenylene and $Y^1$ is isopropylidene in formula (3)), 3,3-bis(4-hydroxyphenyl) phthalimidine, 2-phenyl-3,3'-bis(4-hydroxyphenyl) phthalimidine (also known as N-phenyl phenolphthalein bisphenol, "PPPBP", or 3,3-bis(4-hydroxyphenyl)-2-phenylisoindolin-1-one), 1,1-bis(4-hydroxy-3-methylphenyl)cyclohexane (DMBPC), and from bisphenol A and 1,1-bis(4-hydroxy-3-methylphenyl)-3,3,5-trimethylcyclohexane (isophorone bisphenol).

The polycarbonate can be a linear homopolymer containing bisphenol A carbonate units (BPA-PC); or a branched, cyanophenyl end-capped BPA-PC.

The polycarbonate can be a copolycarbonate. Specific copolycarbonates include those derived from bisphenol A and bulky bisphenol carbonate units, i.e., derived from bisphenols containing at least 12 carbon atoms, for example, 12 to 60 carbon atoms, specifically, 20 to 40 carbon atoms. Examples of such copolycarbonates include copolycarbonates comprising bisphenol A carbonate units and 2-phenyl-3,3'-bis(4-hydroxyphenyl) phthalimidine carbonate units (a BPA-PPPBP copolymer), a copolymer comprising bisphenol A carbonate units and 1,1-bis(4-hydroxy-3-methylphenyl)cyclohexane carbonate units (a BPA-DMBPC copolymer), and a copolymer comprising bisphenol A carbonate units and isophorone bisphenol carbonate units (available, for example, under the trade name APEC from Bayer).

Polycarbonates manufactured and purified as described herein are suitable for use in a wide variety of compositions and applications. Thus, an additive composition can be added, for example, in an extruder, to the polycarbonate to form a polycarbonate composition. The additive composition can comprise one or more additives selected to achieve a desired property, with the proviso that the additive(s) are also selected so as to not significantly adversely affect a desired property of the thermoplastic composition. The additive composition or individual additives can be mixed at a suitable time during the mixing of the components for forming the composition. The additive can be soluble and/or non-soluble in polycarbonate.

The additive composition can include an impact modifier, flow modifier, filler (e.g., a particulate polytetrafluoroethylene (PTFE), glass, carbon, mineral, or metal), reinforcing agent (e.g., glass fibers), antioxidant, heat stabilizer, light stabilizer, ultraviolet (UV) light stabilizer, UV absorbing additive, plasticizer, lubricant, release agent (such as a mold release agent), antistatic agent, anti-fog agent, antimicrobial agent, colorant (e.g., a dye or pigment), surface effect additive, radiation stabilizer, flame retardant, anti-drip agent (e.g., a PTFE-encapsulated styrene-acrylonitrile copolymer (TSAN)), or a combination comprising one or more of the foregoing. For example, a combination of a heat stabilizer, mold release agent, and ultraviolet light stabilizer can be used. In general, the additives are used in the amounts generally known to be effective. For example, the total amount of the additive composition (other than any impact modifier, filler, or reinforcing agent) can be 0.001 to 10.0 weight percent (wt %), or 0.01 to 5 wt %, each based on the total weight of the polymer in the composition.

The polycarbonate can comprise a polyester-polycarbonate copolymer. The polyester-polycarbonate copolymer can comprise a polyarylate such as poly(ethylene terephthalate). The polyester-polycarbonate copolymer can comprise a phthalate-bisphenol carbonate, such as a copolymer derived from ethylene terephthalate and bisphenol A monomers.

The polycarbonate can be manufactured by an interfacial polymerization process. The interfacial polymerization can be a continuous process, a semi-batch process, or a batch process. Although the reaction conditions for interfacial polymerization can vary, an exemplary process generally involves dissolving or dispersing a dihydroxy compound in an aqueous alkali metal hydroxide solution to form a mixture, and adding the resulting mixture to a water immiscible solvent comprising a carbonate compound in the presence of an interfacial catalyst (also referred to as a phase transfer catalyst) such as a tertiary amine, under controlled pH conditions, e.g., 8 to 10.

The aqueous alkali metal hydroxide solution can comprise 20 to 50 wt % of alkali metal hydroxide, specifically, 30 to 40 wt % alkali metal hydroxide based on the total weight of the solution and comprises less than or equal to 20 ppm of an alkali metal chlorate, by weight of the total composition. The alkali metal hydroxide can comprise lithium hydroxide, sodium hydroxide, potassium hydroxide, or a combination comprising at least one of the foregoing. The aqueous alkali metal hydroxide solution can be treated prior to polymerization to reduce chlorate levels. For example, and not by way of limitation, the alkali metal hydroxide solution having reduced chlorate content can be prepared by reacting the alkali metal hydroxide solution with hydrogen and filtering the mixture, for example, through a bed of ruthenium impregnated on carbon.

The water immiscible solvent can comprise an aromatic chlorohydrocarbon and/or an aliphatic chlorohydrocarbon. The solvent can comprise methylene chloride, ethylene dichloride, 1,2-dichloroethane, 1,1,1-trichloroethane, 1,1,2-trichloroethane, chlorobenzene, carbon tetrachloride, toluene, benzene, xylene, anisole, or a combination comprising one or more of the foregoing. The solvent can comprise a low-boiling temperature solvent such as dichloromethane and a high-boiling temperature solvent such as chlorobenzene, for example, in a solvent ratio of 1:2 to 2:1. The aqueous phase can comprise tetrahydrofuran, 1,3/1,4-dioxane, 1,3-dioxolane, water, or a combination comprising one or more of the foregoing.

The carbonate compound can include a carbonyl halide such as carbonyl bromide or carbonyl chloride (phosgene) a bishaloformate of a dihydroxy compound (e.g., the bischloroformate of bisphenol A, hydroquinone ethylene glycol, neopentyl glycol, or the like), and diaryl carbonates. The carbonate compound can comprise phosgene. The carbonate compound can comprise a diaryl carbonate (such as an activated diaryl carbonate). Combinations comprising at least one of the foregoing types of carbonate compounds can also be used. The diaryl carbonate ester can be diphenyl carbonate, or an activated diphenyl carbonate having electron-withdrawing substituents on each aryl, such as bis(4-nitrophenyl)carbonate, bis(2-chlorophenyl)carbonate, bis(4-chlorophenyl)carbonate, bis(methyl salicyl)carbonate, bis (4-methylcarboxylphenyl) carbonate, bis(2-acetylphenyl) carboxylate, bis(4-acetylphenyl) carboxylate, or a combination comprising one or more of the foregoing. An interfacial polymerization reaction to form carbonate linkages can use phosgene as a carbonate compound, and is referred to as a phosgenation reaction.

The interfacial catalyst can comprise a tertiary amine. The tertiary amine can comprise an aliphatic tertiary amine (such as triethylamine and tributylamine), a cycloaliphatic tertiary amine (such as N,N-diethyl-cyclohexylamine), an aromatic tertiary amine (such as N,N-dimethylaniline), or a combination comprising one or more of the foregoing. Among the interfacial catalysts that can be used are catalysts of the formula $(R^3)_4Q^+X$, wherein each $R^3$ is the same or different, and is a $C_{1-10}$ alkyl group; Q is a nitrogen or phosphorus atom; and X is a halogen atom or a $C_{1-8}$ alkoxy group or $C_{6-18}$ aryloxy group. Examples of phase transfer catalysts include $(CH_3(CH_2)_3)_4NX$, $(CH_3(CH_2)_3)_4PX$, $(CH_3(CH_2)_5)_4NX$, $(CH_3(CH_2)_6)_4NX$, $(CH_3(CH_2)_4)_4NX$, $CH_3(CH_3(CH_2)_3)_3NX$, and $CH_3(CH_3(CH_2)_2)_3NX$, wherein X is Cl$^-$, Br$^-$, a $C_{1-8}$ alkoxy group or a $C_{6-18}$ aryloxy group. An effective amount of a phase transfer catalyst can be 0.1 to 10 wt %, or 0.5 to 2 wt %, each based on the weight of dihydroxy compound in the reaction mixture.

Branched polycarbonate blocks can be prepared by adding a branching agent during polymerization. These branching agents include polyfunctional organic compounds containing at least three functional groups selected from hydroxyl, carboxyl, carboxylic anhydride, haloformyl, and mixtures comprising one or more of the foregoing functional groups. The branching agents can comprise trimellitic acid, trimellitic anhydride, trimellitic trichloride, 1,1,1-tris(4-hydroxyphenyl)ethane, tris-p-hydroxy phenyl ethane, isatin-bis-phenol, tris-phenol TC (1,3,5-tris((p-hydroxyphenyeiso-propyl)benzene), tris-phenol PA (4(4(1,1-bis(p-hydroxyphenyl)-ethyl) alpha, alpha-dimethyl benzyl)phenol), trimesic acid, and benzophenone tetracarboxylic acid. The branching agents can be added at a level of 0.05 to 2.0 wt % based on the total weight of the polycarbonate. Combinations comprising linear polycarbonates and branched polycarbonates can be used. The branching agent can be free of a halogenated branching agent, for example, the branching agent can comprise 0 to 0.1 wt % or 0 wt % of a halogenated branching agent based on the total weight of the branching agent.

All types of polycarbonate end groups are contemplated as being useful in the polycarbonate composition, provided that such end groups do not significantly adversely affect desired properties of the compositions. A chain stopper (also referred to as an end capping agent) can be included during polymerization. The chain stopper limits molecular weight growth rate, and so controls molecular weight in the polycarbonate. Examples of chain stoppers include certain mono-phenolic compounds. Mono-phenolic chain stoppers are exemplified by monocyclic phenols such as phenol and $C_{1-22}$ alkyl-substituted phenols such as p-cumyl-phenol, resorcinol monobenzoate, and p- and tertiary-butyl phenol; and monoethers of diphenols, such as p-methoxyphenol. Alkyl-substituted phenols with branched chain alkyl substituents having 8 to 9 carbon atoms can be specifically mentioned. Certain mono-phenolic UV absorbers can also be used as a capping agent, for example, 4-substituted-2-hydroxybenzophenones and their derivatives, aryl salicylates, monoesters of diphenols such as resorcinol monobenzoate, 2-(2-hydroxyaryl)-benzotriazoles and their derivatives, 2-(2-hydroxyaryl)-1,3,5-triazines and their derivatives, and the like. The chain stopper can be free of a halogenated chain stopper, for example, the chain stopper can comprise 0 to 0.1 wt % or 0 wt % of a halogenated chain stopper based on the total weight of the chain stopper.

In general, polymerization of polycarbonate can be performed in a polymerization system that utilizes a polymerization unit, purification section, and an extruder. The polymerization system can comprise a continuously stirred tank reactor(s) (CSTR), a tubular reactor(s), a centrifuge(s) (such as a disc-type centrifuge and a CINC™ centrifuge), a heat exchanger(s), a decanter(s), a separating coalescer(s), an extraction column(s), a devolatilizer(s), an extruder(s), a scrubber(s), a filter(s), or combinations comprising at least one of the foregoing. The polymerization unit can comprise one or more reactors, for example, one or more CSTRs and/or one or more tubular reactors that can each independently act as a polymerization vessel. The reactor(s) can be operated in a batch mode, a semi-batch mode, or a continuous mode. After the polymerization, the polycarbonate can be fed to the purification section to separate the organic phase comprising the polycarbonate from the aqueous phase and to purify the organic phase from impurities such as salts, ions, and the interfacial catalyst. The purification system can comprise a centrifuge(s) (such as a disc-type centrifuge and a CINC™ centrifuge), a heat exchanger(s), a decanter(s), devolatilizer(s), scrubber(s), filter(s), a separating coalescer(s), an extraction column(s), or a combination comprising at least one of the foregoing.

For example, in the purification section, the polycarbonate (for example, that is still in solution) can be fed to a preheater to remove water and/or solvent. The preheater can be any device that allows for heat transfer from a heat transfer medium (such as condensing steam or hot oil) to the polycarbonate. The preheater can be a heat exchanger, for example, a tubular heat exchanger. In the preheater, the polycarbonate is heated to a temperature high enough to lower the residual water in the powder, but low enough to prevent decomposition of the polycarbonate. The temperature of the polycarbonate can be 50 to 320° C., specifically, 75 to 300° C., more specifically, 90 to 300° C., even more specifically, 165 to 250° C.

The polycarbonate can be devolatilized in a devolatization step. The devolatization can comprise a flash devolatization step. The devolatization can comprise a devolatization extrusion. The devolatization can comprise a direct isolation step. The devolatization can comprise a whipped film step. The devolatization can comprise a dewatering extrusion step. The devolatization can comprise a foaming devolatization step. The devolatization can comprise a steam precipitation step. The devolatization can comprise a hot water precipitation step. The devolatization can comprise a gel crush step. The devolatization can comprise a combination comprising one or more of the foregoing devolatization steps. The devolatizing can occur prior to extruding. The devolatization can comprise a devolatization unit with an attached collection pot and melt pump.

After devolatization, the polycarbonate can be dried in one or more dryers (for example, hot air dryers) to convert a wet powder to a dry powder. Examples of dryers are those commercially available from Niro Soavi, S.p.A. of Italy. The polycarbonate exiting a last dryer can comprise less than or equal to 1 wt %, specifically, less than or equal to 0.1 wt % of volatiles based on the total weight of the dried polycarbonate.

The purified polycarbonate can be extruded in an extruder (such as a dewatering extruder and/or a devolatilizing extruder) and subjected to filtration. The filter can be located upstream of and/or downstream of the extruder. It is noted that the polymerization unit can comprise a first and a second parallel line, wherein the first parallel line is connected to the filter located upstream from the extruder, and wherein the second parallel line is connected to a second filter that is located upstream from a second extruder. The extruder can include steam precipitation and methylene chloride devolatilization. The process can comprise an isolation, for example, that produces a wet powder for entry to the extruder.

The polycarbonate compositions have excellent physical properties, including low levels of polymeric chlorine. More specifically, the polycarbonate compositions can have less than or equal to 10 ppm polymeric chlorine, where the polymeric chlorine is present as chlorinated aromatic components in the polymer chain, or less than or equal to 5 ppm, or less than or equal to 3 ppm, or less than or equal to 2 ppm polymeric chlorine based on the total weight of the polycarbonate.

The polycarbonate compositions can also have low levels of extractable ionic chloride, including less than or equal to 10 ppm extractable ionic chloride, or 2 ppm to 5 ppm extractable ionic chloride, or 2 to 2.5 ppm extractable ionic chloride, based on the total weight of the composition.

The polycarbonate compositions can further have a Yellowness Index of a 100 mil (2.54 mm) thick molded plaque of less than 1.5, more specifically, 1 to 1.5, or 1 to 1.3, or 1 to 1.1. Yellowness Index (YI) as used herein is measured in accordance with ASTM D1925-70 (1988).

The polycarbonate compositions can further have low levels of an alkyl amine such as dimethylamine, diethylamine, dibutylamine, or a combination comprising one or more of the foregoing including less than or equal to 1 ppm, more specifically, 0.1 to 1 ppm, or 0.5 to 1 ppm, based on the total weight of the composition. The level of amines can be measured by various methods, for example, by ion chromatography including extraction from the resin powder with deionized water or acidified deionized water.

The method of measuring one or both of a polymeric chlorine and an extractable ionic chloride can comprise first separating the polymeric chlorine from the extractable ionic chloride. For example, the separating can comprise dissolving the polycarbonate in a non-chlorinated solvent, such as tetrahydrofuran (THF) to form a polymer solution. Use of a non-chlorinated solvent can avoid introduction of additional chlorine, which could interfere with subsequent measurements. After dissolving in the non-chlorinated solvent, the polymer solution can be added dropwise to an aqueous solvent at high temperature, such as by adding dropwise to water at a temperature of 90 to 100 degrees Celsius (° C.). The aqueous solvent and temperature of the aqueous solvent, are such that the non-chlorinated solvent can vaporize upon addition and water-soluble ionic chlorides in the polycarbonate can dissolve the aqueous solvent. Desirably, the polymer solution is added dropwise to boiling water. As used herein adding dropwise refers to adding the solution at a rate to ensure that at least 95 wt % of the extractable ionic chloride separates from the polymer solution. Advantageously, droplets, for example, having an average diameter of 0.2 to 10 mm of polymer solution can be added to increase the degree of contact between the polycarbonate polymer and the water and, thus, maximize the separation of the ionic chlorides from the polycarbonate polymer. The polycarbonate can then easily be separated from the aqueous solution (referred to herein as the separated polycarbonate) as the separated polycarbonate generally floats on top of water and can be mechanically collected and dried, for instance in an oven at greater than or equal to 100 degrees Celsius (° C.) to remove residual water. The separated polycarbonate collected after this sample preparation is generally free of the extractable ionic chlorides, which remain in the aqueous solution or water until further manipulation.

The concentration of the polymeric chlorine can be measured by Parr bomb combustion of the separated polycarbonate followed by dissolution of the residue and quantification by ion chromatography. Alternatively or additionally, the polymeric chlorine can be measured by hydrolyzing the separated polycarbonate using sodium or potassium hydroxide and then conducting gas chromatography-mass spectrometry (GC-MS) analysis on the resultant hydrolyzed polycarbonate.

Formula A is an example of aromatic polycarbonate with chlorine in the backbone.

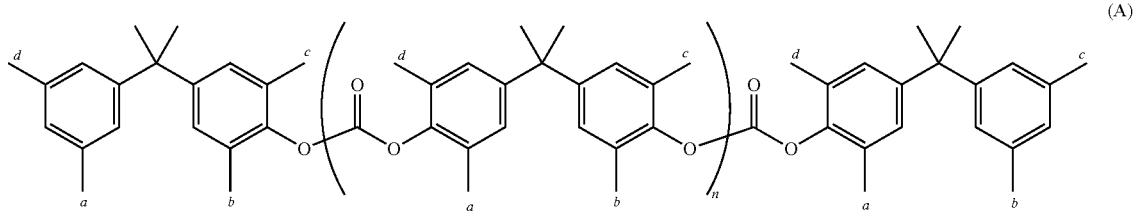

(A)

wherein each of a, b, c and d can, independently, be H or Cl, and wherein at least one of a, b, c and d is Cl.

The thermoplastic compositions are further illustrated by the following non-limiting examples.

EXAMPLES

In the examples, the yellowness index (YI) was determined by a solution based method. Specifically, 3 grams of polycarbonate (LEXAN™ commercially available from SABIC's Innovative Plastic's Business) per sample were aged at 200° C. in a dry oven for 5 hours, and then allowed to cooled to room temperature. The polycarbonate was then dissolved in 20 milliliters (mL) of dichloromethane with the assistance of a wrist shaker. For the ionic chloride studies, a respective amount of sodium chloride was added to the solution of 0.5, 1, and 5 wt % and for the polymeric chlorine samples, chlorinated polycarbonate was used. An X-Rite i7 spectrophotometer was then used to measure the YI color of the solution, where total transmission mode was adopted to measure all the transmitted light and scattered light and the spectrophotometer was operated with the Specular Component included [SCI] with the CE7000A set for Large Area View [LAV]. The measurement time was set at 2.5 seconds and total transmittance apertures was set at 22 mm. This method also used CIE Illuminant C and the CIE 1931

Standard 2° Observer as the default setting. The results were normalized based on the actual concentration of each solution.

Example 1

Four BPA polycarbonate samples (Samples A-D) with an melt volume flow rate (MVR) at 300° C./1.2 kilograms (kg) of 5.1 to 6.9 centimeters cubed per 10 minutes ($cm^3/10$ min) as measured in accordance with ASTM D1238-04, were prepared by an interfacial polymerization. In the preparation of the samples, the polymerization conditions were held constant, where only the amount of sodium chlorate present in the aqueous sodium hydroxide solution (33 wt % sodium hydroxide in water) was changed. For Samples A and B, the sodium hydroxide solution contained less than 10 ppm chlorate by total weight of the sodium hydroxide solution and for samples C and D, the sodium hydroxide solution contained 650 ppm chlorate by total weight of the sodium hydroxide solution.

The BPA polycarbonate samples were collected and dissolved in THF solvent to form polymer solutions. The polymer solutions were added drop wise to respective beakers with boiling water under continuous stirring. The polycarbonate floating on top of the boiling water was collected and placed inside an oven at 100° C.

Properties of Samples A, B, C, and D are summarized in Table 1. In Table 1, the concentration of the polymeric chlorine in the separated polycarbonate was determined by Parr bomb combustion followed by dissolution of the residue and quantification by ion chromatography. The concentration of the extractable ionic chlorine content in the aqueous phase determined by both chromatography and by titration and are Extractable Ionic Chloride and the Undried Chloride in Table 1, respectively.

TABLE 1

| Sample | A | B | C | D |
|---|---|---|---|---|
| Chlorate in NaOH (ppm) | <10 | <10 | 650 | 650 |
| Total Chlorine (ppm) | <10 | <10 | 99 | 111 |
| Extractable Ionic Chloride (ppm) | 2.4 | 2.4 | 43.1 | 53.1 |
| Dried Chloride (ppm) | 0 | 0.8 | 18.4 | 17.4 |
| Undried Chloride (ppm) | 2.3 | 1.6 | 25.3 | 30.6 |
| Diethyl Amine (ppm) | 0.7 | 0.8 | 18.9 | 19.2 |
| Yellowness Index | 1.1 | 1.1 | 5.5 | 3.8 |

Table 1 shows comparative results of polycarbonate resin made using sodium hydroxide with low and high amounts of sodium chlorate. As is shown in Table 1, polycarbonate generated from samples with high levels of chlorate present in the reaction, Samples C and D, had a higher Yellowness Index and higher levels of chlorine and amine compounds.

Example 2

Sample A as described above, corresponding to polycarbonate produced with NaOH with chlorate content below 10 ppm and Sample C as described above, corresponding to polycarbonate produced with NaOH with chlorate content of 650 ppm were subjected to Parr bomb combustion. Specifically, 0.2 grams of the separated polycarbonate samples were subjected to Parr bomb combustion followed by dissolution of the residue and quantification by ion chromatography. An ion chromatograph of Samples A and C is depicted in FIG. 1. A peak at a time of 5.4 minutes shown for Sample C ("C") indicates the presence of chloride on the polymer backbone of the high chlorate content preparation. This result indicates the presence of chlorine atoms instead of hydrogen atoms bonded to the polymer. Sample A corresponding to a low chlorate content sample ("A") does not contain a comparable peak, which indicates absence of chlorine atom bonded to the polymer.

Example 3

Figure 2A:
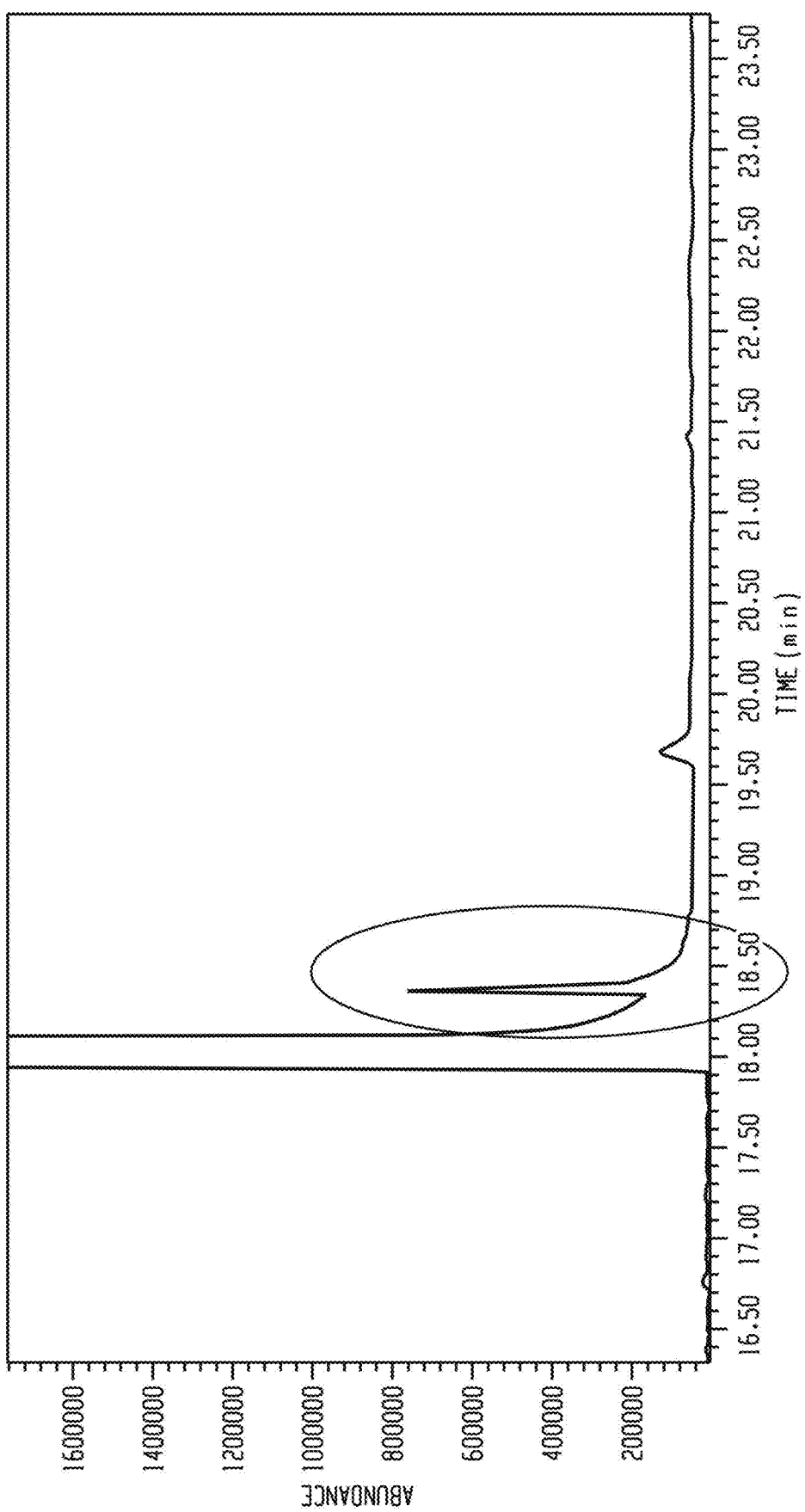
FIG. 2A is a graphical illustration of the gas chromatography data and FIG. 2B is a graphical illustration of the mass spectrometry data.
Figure 2B:
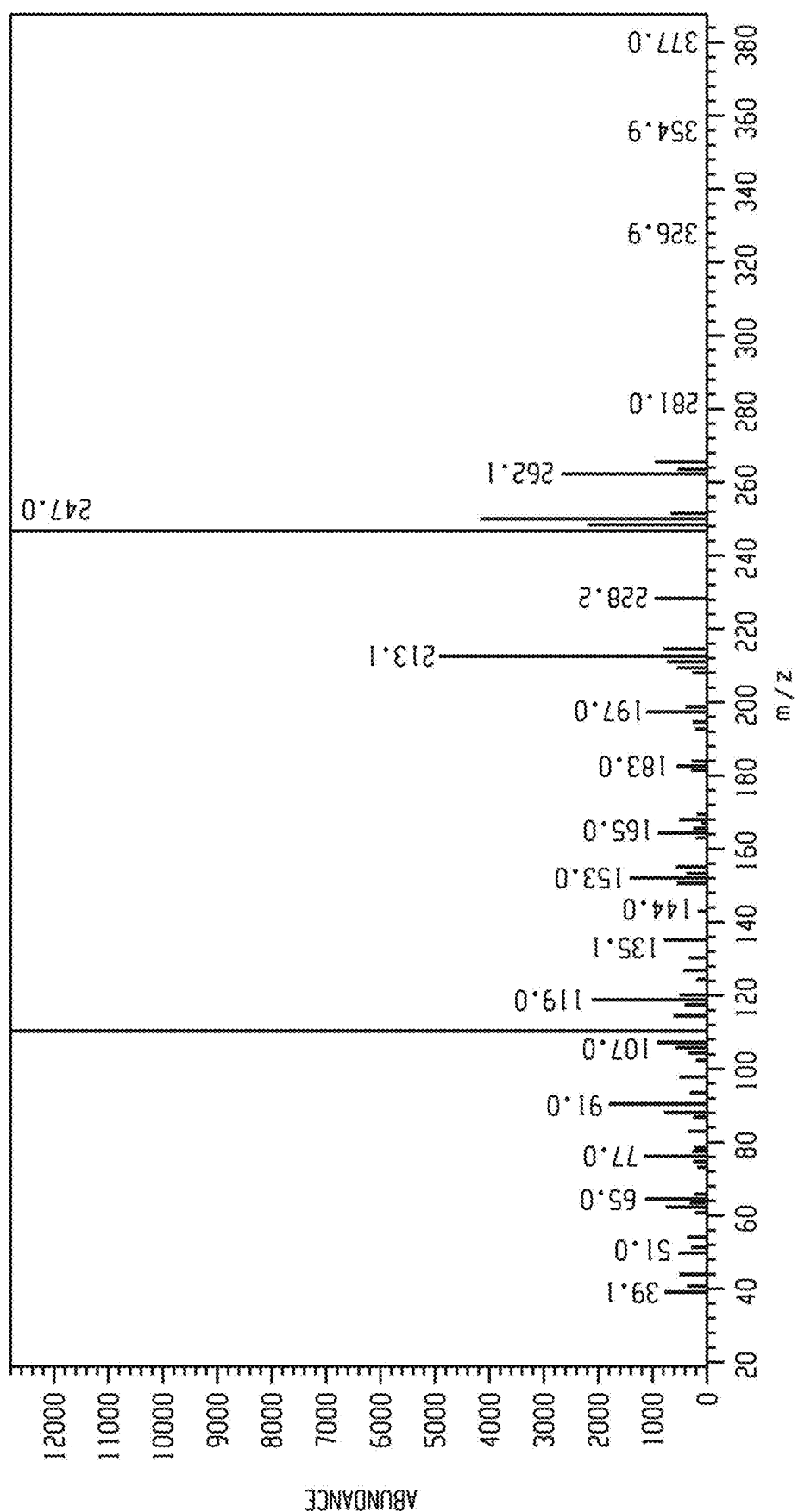

A polycarbonate produced with NaOH with a chlorate content of 650 ppm was hydrolyzed in potassium hydroxide followed by extraction with methanol and then subjected to GC-MS analysis. The results are shown in FIGS. 2A and 2B. The mass spectrometry data taken at a time of 18.4 minutes as shown in FIG. 2A indicates the presence of chlorinated BPA on the polymer backbone, confirming the chlorination of the polycarbonate.

Example 4-11

The effect of ionic inorganic chloride on yellowness index was examined Polycarbonate solutions were prepared by suspending powder polycarbonate, LEXAN™ commercially available from SABIC's Innovative Plastics Business, in solution. The solutions were spiked with 0 wt % NaCl, 0.5 wt % NaCl, 1.0 wt % NaCl, and 5.0 wt % NaCl, Examples 4-7, respectively. The results are shown in Table 2 and FIG. 3.

TABLE 2

| Example | 4 | 5 | 6 | 7 |
|---|---|---|---|---|
| Sodium chloride (wt %) | 0 | 0.5 | 1 | 5 |
| Yellowness index | 1.53 | 1.34 | 1.41 | 1.23 |

Figure 3:
FIG. 3 is a photographical image of polycarbonate solutions with varying amounts of NaCl.

Table 2 and FIG. 3 illustrate that there was no change in yellowness index over a sodium chloride content of 0 to 5 wt %.

Figure 4:
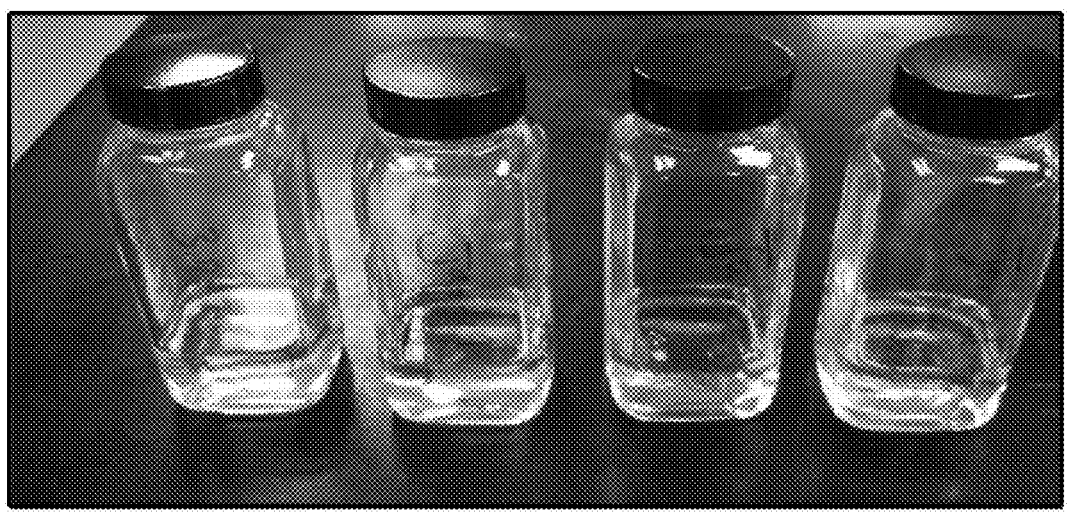
FIG. 4 is a photographical image of polycarbonate solutions with varying amounts of polymeric chlorine.

In order to compare the effect of polymeric chlorine on yellowness index, the same LEXAN™ powder with no chlorine on the polymer backbone, Examples 8 and 9, and with chlorine on the polymer backbone in amounts of 38 ppm and 33 ppm were suspended in solution, Examples 10-11, respectively. The results are shown in Table 3 and FIG. 4.

TABLE 3

| Example | 8 | 9 | 10 | 11 |
|---|---|---|---|---|
| Polymeric chlorine | No | No | Yes | Yes |
| Yellowness index | 1.47 | 1.52 | 8.72 | 8.05 |

Examples 10 and 11 with a chlorinated polycarbonate was observed to have an increased yellowness index of more than 700% as compared to Examples 8 and 9.

Set forth below are some embodiments of the polycarbonate with low chlorine content and a method of making and of analyzing the same.

Embodiment 1: A polycarbonate polymerization process, comprising: analyzing a chlorate content of an alkali metal hydroxide solution, and if the chlorate content is greater than or equal to 20 ppm based on the total weight of the alkali metal hydroxide solution, then reducing the chlorate content in the alkali metal hydroxide solution to a value of less than or equal to 20 ppm chlorate based on the total weight of the alkali metal hydroxide solution prior to interfacially polymerizing; and interfacially polymerizing a phosgene and a dihydroxy compound in the presence of the alkali metal hydroxide solution and an interfacial catalyst to form a polycarbonate.

Embodiment 2: The process of Embodiment 1, further comprising analyzing the polycarbonate to determine at least one of an ionic chloride content and a polymeric chloride content.

Embodiment 3: The process of Embodiment 2, wherein the analyzing of the polycarbonate comprises: dissolving at least a portion of the polycarbonate in a non-chlorinated solvent to form a polycarbonate solution; adding the polycarbonate solution dropwise to boiling water to form a mixture comprising a chloride solution fraction and a polycarbonate fraction, separating the polycarbonate fraction from the chloride solution fraction; measuring at least one of the polymeric chloride content of the polycarbonate fraction and the ionic chloride content of the chloride solution fraction.

Embodiment 4: The process of Embodiment 3, wherein the non-chlorinated solvent comprises tetrahydrofuran.

Embodiment 5: The process of any of Embodiments 3-4, further comprising drying the polycarbonate fraction.

Embodiment 6: The process of any one of Embodiments 3-5, wherein measuring the polymeric chloride content of the polycarbonate fraction comprises: Parr bomb combusting the polycarbonate fraction to obtain a combusted polycarbonate; and conducting ion chromatography on the combusted polycarbonate to determine the polymeric chloride content.

Embodiment 7: The process of any one of Embodiments 3-6, wherein measuring the polymeric chloride content of the polycarbonate fraction comprises: hydrolyzing the polycarbonate fraction to form a hydrolyzed polycarbonate; and conducting gas chromatography-mass spectrometry on the hydrolyzed polycarbonate to determine the polymeric chloride content.

Embodiment 8: The process of any one of the preceding embodiments, comprising the reducing of the chlorate content, wherein the reducing of the chlorate content comprises reducing an ionic chloride content to less than or equal to 10 ppm, or 2 ppm to 5 ppm, or 2 to 2.5 ppm, based on the total weight of the polycarbonate.

Embodiment 9: A polycarbonate made by the process of any one of the preceding embodiments.

Embodiment 10: The polycarbonate of any one of Embodiments 9 and 19-21, wherein the polycarbonate contains less than or equal to 10 ppm chlorinated aromatic components in a polymer chain of the polycarbonate based on the total weight of the polycarbonate.

Embodiment 11: The polycarbonate of any of Embodiments 9-10 and 19-21, wherein the polycarbonate contains less than or equal to 1 ppm, or 0.1 to 1 ppm, or 0.5 to 1 ppm dialkylamine based on the total weight of the polycarbonate.

Embodiment 12: The polycarbonate of any of Embodiments 11 and 19-21, wherein the dialkylamine is at least one of dimethylamine, diethylamine, and dibutylamine.

Embodiment 13: The polycarbonate of any of Embodiments 12 and 19-21, wherein the dialkylamine is dimethylamine.

Embodiment 14: The polycarbonate of any of Embodiments 12 and 19-21, wherein the dialkylamine is diethylamine.

Embodiment 15: The polycarbonate of any of Embodiments 12 and 19-21, wherein the dialkylamine is dibutylamine.

The polycarbonate of any of Embodiments 9-11 and 19-21, wherein the polycarbonate contains less than or equal to 5 ppm ionic chloride based on the total weight of the polycarbonate.

Embodiment 13: The polycarbonate of any of Embodiments 9-12 and 19-21, wherein the polycarbonate has a Yellowness Index measured in accordance with ASTM D1925-70 (1988) of a 2.54 millimeter thickness molded plaque of less than or equal to 1.6 or, less than or equal to 1.3, or 1 to 1.3.

Embodiment 14: The polycarbonate of any of Embodiments 9-13 and 19-21, wherein the polymeric chlorine is present as chlorinated aromatic components in the polymer chain and is present in an amount of less than or equal to 10 ppm, or less than or equal to 5 ppm, or less than or equal to 3 ppm, or less than or equal to 2 ppm based on the total weight of the polycarbonate.

Embodiment 15: An analytical method, comprising: dissolving a polycarbonate, for example, the polycarbonate made by any one of the preceding embodiments, in a non-chlorinated solvent to form a polycarbonate solution; adding the polycarbonate solution dropwise to boiling water to form a mixture comprising a chloride solution fraction and a polycarbonate fraction; separating the polycarbonate fraction from the chloride solution fraction; measuring at least one of a polymeric chloride content of the polycarbonate fraction and a ionic chloride content of the chloride solution fraction.

Embodiment 16: The analytical method of Embodiment 15, wherein measuring the polymeric chloride content comprises: Parr bomb combusting the polycarbonate fraction to obtain a combusted polycarbonate; and conducting ion chromatography on the combusted polycarbonate to determine the polymeric chloride content.

Embodiment 17: The analytical method of any one of Embodiments 15-16, wherein measuring the polymeric chloride content comprises: hydrolyzing the polycarbonate fraction to form a hydrolyzed polycarbonate; and conducting gas chromatography-mass spectrometry on the hydrolyzed polycarbonate to determine the polymeric chloride content.

Embodiment 18: The analytical method of any of Embodiments 15-17, wherein the non-chlorinated solvent comprises tetrahydrofuran.

Embodiment 19: An aromatic polycarbonate, having an aromatic polycarbonate backbone, comprising: less than or equal to 5 ppm of polymeric chlorine attached to the aromatic polycarbonate backbone; less than 0.5 ppm of dichloromethane, less than 5 ppm of monohydric phenols, and less than 0.5 ppm of aromatic compounds containing no chlorine based on the total weight of the aromatic polycarbonate, wherein the aromatic compounds are compounds other than the aromatic polycarbonate.

Embodiment 20: The aromatic polycarbonate according to Embodiment 19, containing: less than 0.01 ppm carbon tetrachloride; less than 2 ppm diaryl carbonates; less than 2 ppm bisphenols; less than 0.05 ppm of alkali metals; less than 0.2 ppm cresols; and less than 200 ppm phenolic OH groups.

Embodiment 21: A polycarbonate polymerization process, comprising: analyzing a chlorate content of an alkali metal hydroxide solution, and, if the chlorate content is greater than or equal to 20 ppm based on the total weight of the alkali metal hydroxide solution, then reducing the chlorate content in the alkali metal hydroxide solution to a value of less than or equal to 20 ppm chlorate based on the total weight of the alkali metal hydroxide solution prior to interfacially polymerizing; and interfacially polymerizing a phosgene and a dihydroxy compound in the presence of the alkali metal hydroxide solution and an interfacial catalyst to form the aromatic polycarbonate of any of Embodiments 19-20.

As used herein, "polymeric chlorine" means chlorine atom bonded to the polycarbonate polymer. "Extractable ionic chloride" as used herein means chloride that can be extracted from the polymer by exposure of the polymer to water or an aqueous solvent.

As used herein, "total chlorine content" means the total chlorine amount in a sample, including chlorine atoms bonded to the polymer and extractable ionic chloride.

As used herein "dried chloride" refers to the extractable ionic chloride measured after drying the polymer at a temperature of greater than or equal to 100° C. and "undried chloride" as used herein refers to the extractable ionic chloride that is measured in the polymer that has not been dried. The concentrations for the dried chloride and the undried chloride are with respect to the polycarbonate composition.

In general, the invention can alternately comprise, consist of, or consist essentially of, any appropriate components herein disclosed. The invention can additionally, or alternatively, be formulated so as to be devoid, or substantially free, of any components, materials, ingredients, adjuvants or species used in the prior art compositions or that are otherwise not necessary to the achievement of the function and/or objectives of the present invention.

All ranges disclosed herein are inclusive of the endpoints, and the endpoints are independently combinable with each other (e.g., ranges of "up to 25 wt %, or, more specifically, 5 to 20 wt %", is inclusive of the endpoints and all intermediate values of the ranges of "5 to 25 wt %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment," "another embodiment," "an embodiment," and so forth, means that a particular element (e.g., feature, structure, and/or characteristic) described in connection with the embodiment is included in at least one embodiment described herein, and may or may not be present in other embodiments. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. Unless otherwise stated, test standards are the most recent as of the filing date of the application.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

In addition, it is to be understood that the described elements can be combined in any suitable manner in the various embodiments.

This application claims priority to U.S. Provisional Application 62/212,178, filed Aug. 31, 2015, which is incorporated herein in its entirety.

As used herein, the term "hydrocarbyl" and "hydrocarbon" refers broadly to a substituent comprising carbon and hydrogen, optionally with 1 to 3 heteroatoms, for example, oxygen, nitrogen, halogen, silicon, sulfur, or a combination thereof; "alkyl" refers to a straight or branched chain, saturated monovalent hydrocarbon group; "alkylene" refers to a straight or branched chain, saturated, divalent hydrocarbon group; "alkylidene" refers to a straight or branched chain, saturated divalent hydrocarbon group, with both valences on a single common carbon atom; "alkenyl" refers to a straight or branched chain monovalent hydrocarbon group having at least two carbons joined by a carbon-carbon double bond; "cycloalkyl" refers to a non-aromatic monovalent monocyclic or multicylic hydrocarbon group having at least three carbon atoms, "cycloalkenyl" refers to a non-aromatic cyclic divalent hydrocarbon group having at least three carbon atoms, with at least one degree of unsaturation; "aryl" refers to an aromatic monovalent group containing only carbon in the aromatic ring or rings; "arylene" refers to an aromatic divalent group containing only carbon in the aromatic ring or rings; "alkylaryl" refers to an aryl group that has been substituted with an alkyl group as defined above, with 4-methylphenyl being an exemplary alkylaryl group; "arylalkyl" refers to an alkyl group that has been substituted with an aryl group as defined above, with benzyl being an exemplary arylalkyl group; "acyl" refers to an alkyl group as defined above with the indicated number of carbon atoms attached through a carbonyl carbon bridge (—C(=O)—); "alkoxy" refers to an alkyl group as defined above with the indicated number of carbon atoms attached through an oxygen bridge (—O—); and "aryloxy" refers to an aryl group as defined above with the indicated number of carbon atoms attached through an oxygen bridge (—O—).

Unless otherwise indicated, each of the foregoing groups can be unsubstituted or substituted, provided that the substitution does not significantly adversely affect synthesis, stability, or use of the compound. The term "substituted" as used herein means that at least one hydrogen on the designated atom or group is replaced with another group, provided that the designated atom's normal valence is not exceeded. When the substituent is oxo (i.e., =O), then two hydrogens on the atom are replaced. Combinations of substituents and/or variables are permissible provided that the substitutions do not significantly adversely affect synthesis or use of the compound. Exemplary groups that can be present on a "substituted" position include, but are not limited to, cyano; hydroxyl; nitro; azido; alkanoyl (such as a $C_{2-6}$ alkanoyl group such as acyl); carboxamido; $C_{1-6}$ or $C_{1-3}$ alkyl, cycloalkyl, alkenyl, and alkynyl (including groups having at least one unsaturated linkages and from 2 to 8, or 2 to 6 carbon atoms); $C_{1-6}$ or $C_{1-3}$ alkoxys; $C_{6-10}$ aryloxy such as phenoxy; $C_{1-6}$ alkylthio; $C_{1-6}$ or $C_{1-3}$ alkylsulfinyl; $C_{1-6}$ or $C_{1-3}$ alkylsulfonyl; aminodi($C_{1-6}$ or $C_{1-3}$) alkyl; $C_{6-12}$ aryl having at least one aromatic rings (e.g., phenyl, biphenyl, naphthyl, or the like, each ring either substituted or unsubstituted aromatic); $C_{7-19}$ arylalkyl having 1 to 3 separate or fused rings and from 6 to 18 ring carbon atoms; or arylalkoxy having 1 to 3 separate or fused rings and from 6 to 18 ring carbon atoms, with benzyloxy being an exemplary arylalkoxy.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

We claim:

1. An aromatic polycarbonate, having an aromatic polycarbonate backbone, comprising:
    less than or equal to 5 ppm of polymeric chlorine attached to the aromatic polycarbonate backbone;
    less than 0.5 ppm of dichloromethane,
    less than 5 ppm of monohydric phenols, and
    less than 0.5 ppm of aromatic compounds containing no chlorine based on the total weight of the aromatic polycarbonate, wherein the aromatic compounds are compounds other than the aromatic polycarbonate.

2. The aromatic polycarbonate according to claim 1, containing:
    less than 0.01 ppm carbon tetrachloride;
    less than 2 ppm diaryl carbonates;
    less than 2 ppm bisphenols;
    less than 0.05 ppm of alkali metals;
    less than 0.2 ppm cresols; and
    less than 200 ppm phenolic OH groups.

3. The polycarbonate according to claim 1, wherein the polycarbonate contains less than or equal to 10 ppm chlorinated aromatic components in a polymer chain of the polycarbonate based on the total weight of the polycarbonate.

4. The polycarbonate according to claim 1, wherein the polycarbonate contains less than or equal to 1 ppm dialkylamine based on the total weight of the polycarbonate.

5. The polycarbonate according to claim 1, wherein the dialkylamine is at least one of dimethylamine, diethylamine, and dibutylamine.

6. The polycarbonate according to claim 1, wherein the dialkylamine is dimethylamine.

7. The polycarbonate according to claim 1, wherein the dialkylamine is diethylamine.

8. The polycarbonate according to claim 1, wherein the dialkylamine is dibutylamine.

9. The polycarbonate according to claim 1, wherein the polycarbonate contains less than or equal to 5 ppm ionic chloride based on the total weight of the polycarbonate.

10. A polycarbonate polymerization process, comprising:
    analyzing a chlorate content of an alkali metal hydroxide solution, and, if the chlorate content is greater than or equal to 20 ppm based on the total weight of the alkali metal hydroxide solution, then reducing the chlorate content in the alkali metal hydroxide solution to a value of less than or equal to 20 ppm chlorate based on the total weight of the alkali metal hydroxide solution prior to interfacially polymerizing; and
    interfacially polymerizing a phosgene and a dihydroxy compound in the presence of the alkali metal hydroxide solution and an interfacial catalyst to form the aromatic polycarbonate according to claim 1.

11. The process of claim 10, further comprising analyzing the polycarbonate to determine at least one of an ionic chloride content and a polymeric chloride content.

12. The process of claim 11, wherein the analyzing of the polycarbonate comprises: dissolving at least a portion of the polycarbonate in a non-chlorinated solvent to form a polycarbonate solution; adding the polycarbonate solution dropwise to boiling water to form a mixture comprising a chloride solution fraction and a polycarbonate fraction, separating the polycarbonate fraction from the chloride solution fraction; measuring at least one of the polymeric chloride content of the polycarbonate fraction and the ionic chloride content of the chloride solution fraction.

13. The process of claim 12, wherein the non-chlorinated solvent comprises tetrahydrofuran.

14. The process according to claim 12, wherein measuring the polymeric chloride content of the polycarbonate fraction comprises: Parr bomb combusting the polycarbonate fraction to obtain a combusted polycarbonate; and conducting ion chromatography on the combusted polycarbonate to determine the polymeric chloride content.

15. The process according to claim 12, wherein measuring the polymeric chloride content of the polycarbonate fraction comprises: hydrolyzing the polycarbonate fraction to form a hydrolyzed polycarbonate; and conducting gas chromatography-mass spectrometry on the hydrolyzed polycarbonate to determine the polymeric chloride content.

16. The process according to claim 10, comprising the reducing of the chlorate content, wherein the reducing of the chlorate content comprises reducing an ionic chloride content to less than or equal to 10 ppm, based on the total weight of the polycarbonate.

17. An analytical method, comprising: dissolving a polycarbonate, for example, the polycarbonate made by any claim 1, in a non-chlorinated solvent to form a polycarbonate solution; adding the polycarbonate solution dropwise to boiling water to form a mixture comprising a chloride solution fraction and a polycarbonate fraction; separating the polycarbonate fraction from the chloride solution fraction; measuring at least one of a polymeric chloride content of the polycarbonate fraction and a ionic chloride content of the chloride solution fraction.

18. The analytical method of claim 17, wherein measuring the polymeric chloride content comprises: Parr bomb combusting the polycarbonate fraction to obtain a combusted polycarbonate; and conducting ion chromatography on the combusted polycarbonate to determine the polymeric chloride content.

19. The analytical method according to claim 17, wherein measuring the polymeric chloride content comprises: hydrolyzing the polycarbonate fraction to form a hydrolyzed polycarbonate; and conducting gas chromatography-mass spectrometry on the hydrolyzed polycarbonate to determine the polymeric chloride content.

20. The analytical method according to claim 17, wherein the non-chlorinated solvent comprises tetrahydrofuran.

* * * * *